United States Patent
El Hadri et al.

(10) Patent No.: US 6,890,955 B2
(45) Date of Patent: May 10, 2005

(54) ARYLOXYPROPANOLAMINE DERIVATIVES, METHOD OF PREPARATION AND APPLICATIONS THEREOF

(75) Inventors: Ahmed El Hadri, Morsang sur Orge (FR); Philippe Archimbault, Monaco (MC); Gérard Leclerc, Grenoble (FR); Arthur Donny Strosberg, Paris (FR); France Pietri-Rouxel, Nozay (FR)

(73) Assignee: Virbac SA, Carros (FR)

( * ) Notice: Subject to any disclaimer, the term of this patent is extended or adjusted under 35 U.S.C. 154(b) by 0 days.

(21) Appl. No.: 10/336,001

(22) Filed: Jan. 3, 2003

(65) Prior Publication Data

US 2003/0158259 A1 Aug. 21, 2003

Related U.S. Application Data

(62) Division of application No. 09/934,487, filed on Aug. 23, 2001, now abandoned, which is a continuation of application No. 09/297,604, filed as application No. PCT/FR97/01963 on Nov. 3, 1997, now abandoned.

(30) Foreign Application Priority Data

Nov. 5, 1996 (FR) ............................... 96 13438

(51) Int. Cl.$^7$ .................. A61K 31/195; C07D 317/48; C07C 229/34

(52) U.S. Cl. ................ 514/567; 514/452; 514/467; 549/440; 562/442; 558/422

(58) Field of Search .................. 549/440; 562/442; 514/567, 452, 467; 558/422

(56) References Cited

PUBLICATIONS

The Surgeon General's Report on Nutrition and Health (1988) U.S. Dept. of Health and Human Services, DHHS (PHS) Publication # 88–50210.*

* cited by examiner

Primary Examiner—James O. Wilson
Assistant Examiner—Ebenezer Sackey
(74) Attorney, Agent, or Firm—Morgan Lewis & Bockius LLP

(57) ABSTRACT

The invention concerns aryloxypropanolamine derivatives having at least an anti-diabetic and anti-fat activity and their methods of preparation and applications, particularly as human and veterinary medicine and animal food additive. These derivatives comply with the general formula (I) in which $R_2$ represents one of the following groups: —$CH_2$—, —$CH_2$—$CH_2$, —$CH(CH_3)$—$CH_2$—, —$C(CH_3)$=$CH$—, —$C(CH_3)_2$—$CH_2$— or a bond; Q represents: (i) a phenyl radical 3,4-disubstituted alkylene dioxy determining with the phenyl radical, a non-substituted benzodioxane unit, a non-substituted benzodioxol unit, or a 2-substituted benzodioxol unit, (ii) a phenyl radical 3 and/or 4-substituted, by a O—$(CH_2)_x$—$COOR_5$ group, (iii) a condensed polycyclic hydrocarbon comprising at least two condensed cycles, (iv) a cyclic hydrocarbon system, optionally cross-linked, and constituting a cycloalkane comprising 1, 2 or 3 cycles

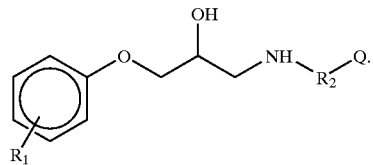

(I)

8 Claims, No Drawings

ARYLOXYPROPANOLAMINE DERIVATIVES, METHOD OF PREPARATION AND APPLICATIONS THEREOF

This is a divisional of application Ser. No. 09/934,487 filed on Aug. 23, 2001, which is a continuation of application Ser. No. 09/297,604 filed May 5, 1999, now abandoned, which is a 371 of PCT/FR97/01963, filed Nov. 3, 1997, all of which are herein incorporated by reference in their entirety.

The present invention relates to aryloxypropanolamine derivatives possessing at least antidiabetic and antiobesity activity, to the methods for their preparation and to their applications, especially as drugs in human and veterinary medicine and as animal feed additives.

There are two major forms of diabetes in existence, namely type I or insulin-dependent diabetes, which results from a complete insulin deficiency, and type II or insulin-independent diabetes, which often appears in the presence of normal or even slightly raised insulin levels and seems to be the result of an inability of the tissues to respond appropriately to the presence of insulin, due to metabolic anomalies in glucose production and utilization; such anomalies prevent the maintenance of a physiological blood glucose level, resulting in hyperglycaemia. The majority of type II diabetics are also obese.

In addition to special diets, the customary methods of treating type II diabetes and obesity include the use of β-adrenergic agents and more particularly $\beta_3$-adrenergic agents (agonists), which stimulate lipolysis.

Compounds which stimulate the $\beta_3$-adrenergic receptors also possess antiobesity activity. They further possess hypoglycaemic (antihyperglycaemic) and antidiabetic activity, although the mechanism of this effect does not seem to be known.

The following may be mentioned among the products possessing $\beta_3$-adrenergic activity:

phenylethanolamines (U.S. Pat. No. 4,478,849 in the name of Ainsworth et al.; U.S. Pat. No. 5,106,867 in the name of Bloom et al.; article published in Drugs Fut., 1993, 18(6) 541), which are considered to have antiobesity, antidiabetic and antihyperglycaemic activity;

phenoxypropanolamines substituted on the nitrogen by ether groups of the aryloxyalkyl type (European patents 0 210 849 and 0 254 532), which compounds are considered to have essentially antiobesity activity; phenoxypropanolamines substituted by a phenylsulfonamide joined to the amine group by one of the following groups: —CH$_2$—, —CH$_2$—CH$_2$—, —CH═CH or —CH$_2$O— (European patent 0 611 003), which compounds are considered to be active in the treatment of type II diabetes and obesity and as antidepressants; phenoxypropanolamines substituted by a 1,3-benzodioxole-2,2-dicarboxylic acid group (U.S. Pat. No. 5,488,064) joined to the amine group by the following group:

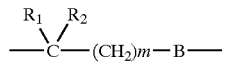

in which B is a bond or an oxygen atom, m is equal to 1 or 2 and $R_1$ and $R_2$, which are identical or different, are a hydrogen atom or a lower alkyl group, which compounds are considered to have not only antidiabetic activity but also antiobesity activity and activity on intestinal hypermotility disorders, depression and stress, regulation of the intraocular pressure, hypertriglyceridaemia, hypercholesterolaemia, atherosclerosis and cardiovascular diseases.

Consequently the above-mentioned compounds have the major disadvantage of not being selective towards the $\beta_3$-adrenergic receptor, so they can exhibit activity towards the $\beta_1$- and/or $\beta_2$-adrenergic receptors; in particular, the broad spectrum of activity of the compounds described in U.S. Pat. No. 5,488,064 can lead to unfavourable side effects in the respiratory and/or cardiac system.

The Applicant consequently set itself the task of providing compounds which possess selective $\beta_3$-adrenergic activity and meet practical needs better than the compounds of the prior art.

In fact, a compound which stimulates the $\beta_3$-adrenergic receptors selectively, i.e. which has only small $\beta_1$ or $\beta_2$ effects, if any, will have the desired antidiabetic and/or antiobesity activity without the unwanted effects associated with concomitant $\beta_1$ stimulation (increase in heart rate) or $\beta_2$ stimulation (muscle tremors).

The selectivity of such compounds can be determined by carrying out binding studies on CHO-bovine K1 $\beta_3$ cells according to the protocol described in Eur. J. Biochem., 1995, 230, 350–358 (F. Pietri-Rouxel et al.); the products are tested on the whole cells, at a maximum concentration of 10 μmolar, for their capacity to stimulate the accumulation of cAMP (agonist) or to inhibit the accumulation stimulated by a concentration (10 nM) of isoproterenol (antagonist).

The present invention relates to compounds of general formula I below:

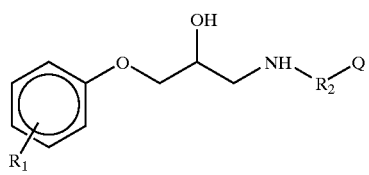

in which:
$R_1$, a substituent in the 2-, 3- or 4-position of the phenyl group, is a hydrogen atom, a halogen atom or one of the following groups: hydroxyl; $C_1$–$C_{10}$ lower alkyl selected in particular from methyl, ethyl, propyl, isopropyl, butyl and tert-butyl groups; $C_1$–$C_{10}$-alkoxy, especially methoxy; benzyloxy; nitro; cyano; trifluoromethyl; or amino optionally substituted (monosubstituted or disubstituted) by 1 or 2 lower alkyl radicals as defined above;
$R_2$ is one of the following groups: —CH$_2$—, —CH$_2$—CH$_2$—, —CH(CH$_3$)—CH$_2$—, —C(CH$_3$)═CH—, —C(CH$_3$)$_2$—CH$_2$—, or a bond; and
Q is:
(i) a phenyl radical 3,4-disubstituted by alkylenedioxy, which forms, with the phenyl radical, an unsubstituted benzodioxane unit, an unsubstituted benzodioxole unit or a benzodioxole unit 2-substituted by two radicals $R_3$ and $R_4$ according to the following formula:

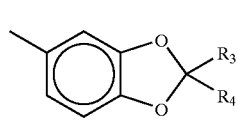

in which $R_3$ and $R_4$ are independently selected from the group comprising a hydrogen atom and a hydroxymethyl group;
(ii) a 3- and/or 4-substituted phenyl radical of formula II below:

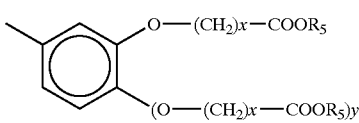
(formula II)

in which:

$R_5$ is a hydrogen atom or a linear or branched $C_1$–$C_6$ lower alkyl radical;

x is an integer between 1 and 3; and y is 0 or 1;

(iii) a fused polycyclic hydrocarbon comprising at least two fused rings and selected from the following units: indene, indacene, naphthalene, azulene, biphenylene, acenaphthylene, fluorene, phenalene, phenanthrene and anthracene; or (iv) an optionally bridged, cyclic hydrocarbon system which consists of a cycloalkane comprising 1, 2 or 3 rings optionally containing substituents selected from methyl, ethyl, isopropyl, propyl, butyl and tert-butyl groups, the main ring containing 5 or 6 members.

By way of example, cycloalkane with one ring is understood as meaning a cyclopentane or a cyclohexane, cycloalkane with two rings is understood as meaning terpenes, and cycloalkane with three rings is understood as meaning especially adamantanes.

The compounds of formula (I) also include the pharmacologically acceptable salts of these derivatives, as well as all the optical isomers and their components or mixtures of diastereoisomers. The basic products according to the present invention can be salified with the customary mineral acids and also with the organic acids in common use, such as tartaric, maleic, malonic, fumaric, succinic, methanesulfonic, ethenesulfonic and hydroxyethanesulfonic acids. The derivatives of acid character can be salified with pharmacologically acceptable mineral bases such as alkali metal or alkaline earth metal reagents, or with non-toxic organic bases such as aliphatic amines, amino alcohols or the like.

The following may be mentioned among the preferred compounds of formula (I):

the compounds comprising an unsubstituted benzodioxole:

⇒ of the following formula:

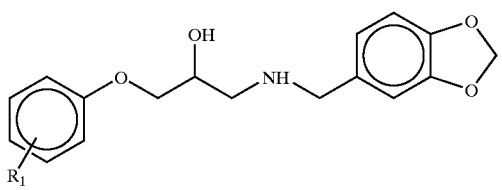

in which $R_1$ is a hydrogen atom, a methoxy or a chlorine atom in the para position, or a chlorine atom, a hydroxyl group, a nitro group, a cyano group or a trifluoromethyl group in the meta position; or ⇒ of the following formula:

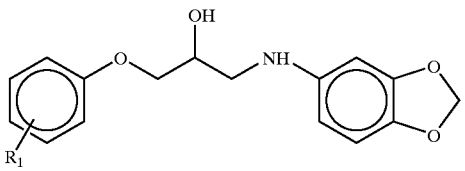

in which $R_1$ is a hydrogen atom or a methoxy group in the para position;

the compound of the following formula:

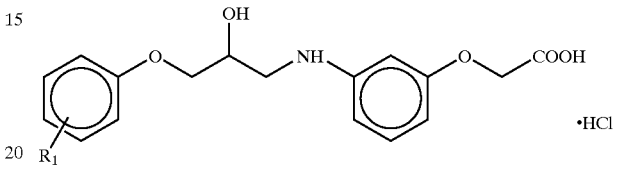

in which $R_1$ is a hydrogen atom;

the compound of the following formula:

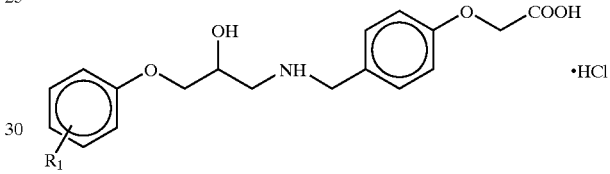

in which $R_1$ is a hydrogen atom; and the compounds in which:

$R_1$ is a hydrogen atom, a 4-O-methyl, a 3-OH or a trifluoromethyl group;

$R_2$ is a bond or one of the following groups: —$CH_2$— or —$CH_2$—$CH_2$—; and Q is a fluorene group or a cyclic hydrocarbon system, for example a cyclohexyl, a 1-adamantyl group or a 2-adamantyl group.

The compounds of formula (I) can be prepared by reacting:

a phenoxyepoxypropane compound of formula III:

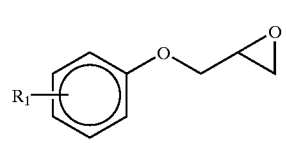
(formula III)

in which $R_1$ is as defined above, with a primary amine of formula (IV):

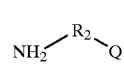
(formula IV)

in which $R_2$ and Q are as defined above.

Some compounds of formula (III) are commercially available; otherwise they can be prepared by reacting a phenol, appropriately chosen in terms of the identity of $R_1$, with an epichlorohydrin or an epibromohydrin in the presence of a halogen acceptor, preferably in a polar solvent. If the nature of the substituent $R_1$ makes it sensitive to this condensation reaction, it is preferably protected before the reaction by an appropriate technique, for example as described in "Protective Groups in Organic Synthesis, 2nd edition, T. W. Greene and P. G. M. Wuts, John Wiley and Sons, New York, 1991".

Some compounds of formula (IV) are commercially available; others can be prepared by different methods, including the one shown below for the case of a product of formula (I) in which Q is a group of formula (II).

The method of preparation is illustrated in scheme 1 below:

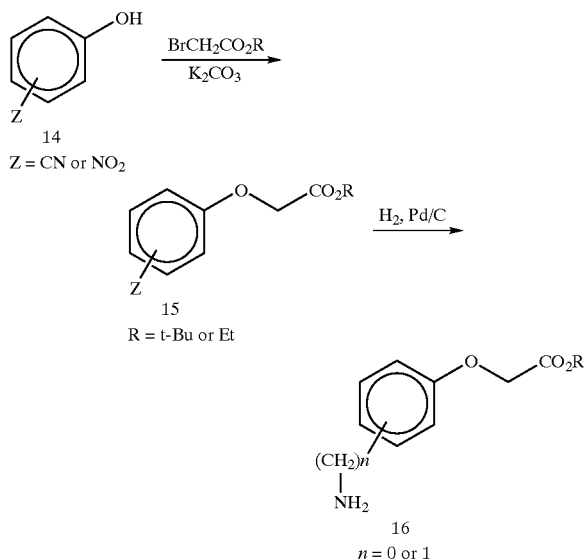

The treatment of nitrophenol (or cyanophenol) 14 with tert-butyl bromoacetate and anhydrous potassium carbonate in acetone gives the product 15, which is hydrogenated in the presence of Pd/C (10%) to give the amine 16 (scheme 1). If Z is a cyano group, the catalytic reduction in the presence of PdcC produces monobenzylanine and dibenzylamine derivatives.

The intermediates of formula (III) and of formula (IV), $NH_2$—$R_2$—Q, are coupled by heating (in the crude form or dissolved in a polar solvent such as anhydrous dimethylformamide) for 12 to 14 hours, at a temperature between 70 and 100° C., to give compounds of formula (I). Some compounds of formula (I) are obtained with one or two ester groups, which react respectively with 6 N HCl at 80° C. for 12 hours and with 1 N NaOH at room temperature for 12 to 48 hours to give the carboxylic acid salt, as illustrated in scheme 2:

Scheme 2

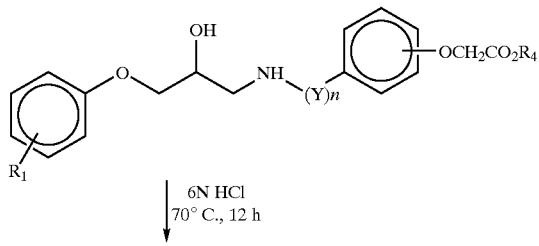

$R_4$ = tert-butyl or Et
$(Y)n$ = bond
$(Y)n$ = $CH_2$

The compounds of formula (I) have a particularly valuable activity as $\beta_3$-adrenergic receptor agonists; in particular, they possess a valuable action on thermogenesis and can therefore be used in the treatment of obesity or in metabolic function disorders. In certain cases, they can also modify fat catabolism and be used in animal rearing, improving the production of muscle rather than fat.

These compounds can be employed in animal feeding to avoid an unprofitable fattening of the animals and instead to promote an increase in muscle bulk.

As their $\beta_3$ activity manifests itself essentially on the smooth muscle, moderation of the intestinal contraction does not therefore occur to the detriment of a cardiovascular effect.

A preparation containing at least one product of formula (I) according to the invention can be administered to animals, including man, suffering from diabetes, obesity or intestinal motility disorder.

The products according to the invention are preferably administered orally or sublingually, but other routes of administration can also be used (intranasal route, transdermal route, parenteral routes such as subcutaneous, intravenous and intraperitoneal routes).

The doses administered vary from case to case between 0.1 and 100 mg/kg of live weight, preferably between 1 and 10 mg/kg of live weight.

If necessary, the compounds of formula (I) can be administered in combination with $\beta_1$- or $\beta_2$-adrenergic products.

In the treatment of obesity, which may be associated with a treatment for diabetes, these products are administered at doses of 1 to 10 mg/kg of body weight; in the case of administration to animals, appropriate pharmaceutical forms can be employed according to the species and include especially solutions for spreading over the animal's body (solution for spreading by hand, solution for spreading by vaporization, etc.).

The compounds of the present invention are formulated as tablets, ordinary capsules, gelatin capsules or syrup for oral administration. These gelatin capsule, ordinary capsule and tablet forms can contain excipients conventionally used in pharmaceutical formulation, such as adjuvants or binders like starches, gums and gelatin, adjuvants like calcium phosphate, disintegrating agents like cornstarch or alginic acids, a lubricant like magnesium stearate, sweeteners or flavourings. Solutions or suspensions can be prepared in aqueous or non-aqueous media by the addition of pharmacologically compatible solvents. These include glycols, polyglycols, propylene glycols, polyglycol ether, DMSO and ethanol.

They can also be formulated as sterile suspensions or solutions for parenteral or intranasal administration, or they can be presented as skin patches. The unit dose of between 1 and 500 mg of the compound of formula (I) is mixed with an excipient appropriate to the form produced: solvent, diluent, excipient, preservative, sweetener or perfume. The amount of active principle present in each unit dose is such that it can be administered one or more times throughout the day. Programmed release formulations can also be prepared to give a long-lasting effect, making it possible to increase the treatment intervals.

The Examples given illustrate the content of the invention without limiting its scope only to the Examples described.

EXAMPLE 1

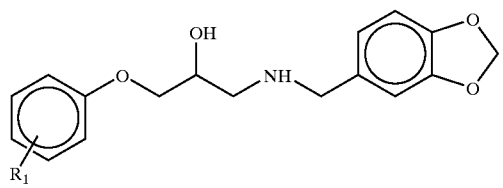

N-((1,3-Benzodioxol-5-yl)methyl)-2-hydroxy-3-(3-hydroxyphenoxy)propylamine 1e 36.6 g (332.40 mmol) of resorcinol and 42 g (331.78 mmol) of benzyl chloride are refluxed overnight in 250 ml of dry $Me_2CO$ in the presence of 46.6 g of $K_2CO_3$, with stirring. The mixture is cooled, filtered and evaporated. The residue obtained is diluted in 500 ml of water and extracted with ethanol. The organic layer is washed with 10% aqueous NaOH and extracted with ethanol. The red oil obtained is distilled with the aid of a bulb tube distillation apparatus to give 18 g of m-$PhCH_2OC_6H_4OH$, b.p.$_{15}$ 240–245° C. (lit. b.p.$_{11}$ 202–210° C.). A solution of 3.3 g (16.5 mmol) of m-$PhCH_2OC_6H_4OH$ in 50 ml of DMF is treated with 0.8 g (16.5 mmol) of sodium hydride and the mixture is stirred for 15 minutes. After the addition of 13.75 ml (16.5 mmol) of epichlorohydrin, the mixture is stirred at 60° C. for one hour until alkylation is complete. The excess reagent and the solvent are evaporated off under reduced pressure and the residue is partitioned between the following two phases: ethyl acetate and water. The organic phase yields the epoxide, which is used without further purification.

The epoxide is dissolved in DMF containing one equivalent of amine and heated overnight at 80° C. After cooling, the solvent is removed under vacuum and the oily residue is chromatographed on a silica gel column using a mixture of solvents, and recrystallized as indicated in Table 1.

TABLE I

Chemical data of the compounds I

| Compound | $R_1$ | Yield % | Crystallization solvent | Melting point ° C. |
|---|---|---|---|---|
| I1a | H | 67 | MeOH | 102–103 |
| I1b | p-$OCH_3$ | 80 | MeOH | 107–108 |
| I1c | m-Cl | 62 | MeOH | 128–129 |
| I1d | p-Cl | 74 | EtOH | 98–99 |
| I1e | m-OH | 62 | $CH_3CN$ | 230–231 |
| I1f | m-$NO_2$ | 47 | MeOH | 129–130 |
| I1g | m-CN | 55 | MeOH | 138–139 |
| I1h | m-$CF_3$ | 39 | MeOH | 121–122 |

The $^1H$ NMR spectra ($\delta$) of the compounds of Example 1 are illustrated below:

Compound 1a (free base), $\delta$ (ppm): 2.59 (m, 2H), 3.62 (s, 2H), 3.90 (m, 3H), 5.95 (s, 2H), 6.78 (m, 2H Ar), 6.90 (m, 4H Ar), 7.26 (dt, 2H Ar, J=7.73, 1.02 Hz).

Compound 1b (free base), $\delta$ (ppm): 2.52 (m, 2H), 3.61 (s, 2H), 3.68 (s, 3H), 3.83 (n, 3H), 4.88 (b, NH), 5.95 (s, 2H), 6.75 (dd, 1H Ar, J=8.0, 1.38 Hz), 6.81 (d, 1H Ar, J=8.0 Hz), 6.83 (s, 4H), 6.89 (d, 1H Ar, J=1.1 Hz).

Compound 1c (maleate), $\delta$ (ppm): 2.90 (dd, 1H, J=13.56, 9.40 Hz), 3.07 (dd, 1H, J=12.59, 2.94 Hz), 3.97 (d, 2H, J=5.07 Hz), 4.10 (s, 2H), 4.12 (m, 1H), 6.01 (s, 2H), 6.04 (s, 2H), 6.90 (dd, 1H Ar, J=8.31, 2.14 Hz), 7.00 (m, 4H Ar), 7.09 (s, 1H Ar), 7.31 (t, 1H Ar, J=8.42 Hz).

Compound 1d (maleate), $\delta$ (ppm): 2.90 (dd, 1H, J=12.63, 9.20 Hz), 3.08 (dd, 1H, J=12.67, 3.18 Hz), 3.93 (d, 2H, J=5.18 Hz), 4.10 (s, 2H), 4.12 (m, 2H), 6.03 (s, 2H), 6.04 (s, 2H), 6.95 (m, 4H Ar), 7.09 (s, 1H), 7.34 (d, 2H, J=8.99 Hz).

Compound 1e (free base), $\delta$ (ppm): 2.85 (dd, 1H, J=12.47, 8.89 Hz), 3.04 (dd, 1H, J=12.63, 3.02 Hz), 3.93 (d, 2H, J=5.18 Hz), 4.07 (s, 2H), 4.23 (m, 1H), 5.85 (m, 1H Ar), 6.03 (s, 2H), 6.53 (m, 2H Ar), 6.92 (d, 1H Ar, J=8.0 Hz), 7.02 (dd, 1H Ar, J=8.0, 1.58 Hz), 7.19 (n 2H Ar).

Compound 1f (free base), $\delta$ (ppm): 2.58 (t, 2H, J=5.64 Hz), 3.62 (s, 2H), 3.89 (m, 1H), 3.97 (dd, 1H, J=15.59, 5.98 Hz), 4.11 (dd, 1H, J=15.14, 4.0 Hz), 4.99 (b, 1H), 5.94 (s, 2H), 6.78 (m, 2H), 6.89 (s, 1H), 7.39 (ddd, 1H, J=8.29, 2.47, 0.95 Hz), 7.55 (dd, 1H, J=6.93, 1.05 Hz).

Compound 1g (free base), $\delta$ (ppm): 2.55 (m, 2H), 3.61 (s, 2H), 3.89–4.05 (m, 3H), 4.97 (s, 1H), 5.95 (s, 2H), 6.72–6.78 (m, 2H), 6.88 (s, 1H), 7.24–7.50 (m, 4H).

Compound 1h (free base), $\delta$ (ppm): 2.58 (m, 2H), 3.61 (s, 2H), 3.90–4.05 (m, 3H), 4.97 (s, 1H), 5.94 (s, 2H), 6.72–6.78 (m, 2H), 6.89 (s, 1H), 7.20–7.27 (m, 3H), 7.49 (t, 1H, J=7.69 Hz).

EXAMPLE 2

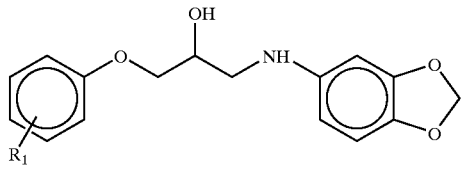

N-(Benzodioxol-5-yl)-2-hydroxy-3-(alkoxyphenoxy)propylamine

Analogously to Example 1, the compounds of Example 2 are prepared from a commercially available epoxide.

The chemical properties and the NMR spectra of these products are illustrated below:

TABLE II

Chemical data of the compounds of Example 2

| Compound | $R_1$ | Yield % | Solvent | Melting point ° C. |
|---|---|---|---|---|
| 2a | H | 45 | EtOAc/cyclohex (2/8) | 80–81 |
| 2b | p-OMe | 65 | $Et_2O$/cyclohex | 80–81 |

$^1H$ NMR spectra ($\delta$) of the compounds 2

Compound 2a (free base), $\delta$ (ppm): 3.22 (dd, 1H, J=12.77, 7.02 Hz), 3.37 (dd, 1H, J=12.76, 4.21 Hz), 4.05 (m, 2H), 4.22 (m, 1H), 5.86 (s, 2H), 6.11 (dd, 1H Ar, J=8.26, 2.27 Hz), 6.32 (d, 1H Ar, J=2.25 Hz), 6.66 (d, 1H Ar, J=8.26 Hz), 6.96 (m, 3H Ar), 7.30 (m, 2H Ar).

Compound 2b (free base), $\delta$ (ppm): 3.21 (dd, 1H, J=12.75, 7.07 Hz), 3.35 (dd, 1H, J=12.73, 4.22 Hz), 3.78 (s, 3H), 3.97 (dd, 1H, J=9.55, 6.06 Hz), 4.03 (dd, 1H, J=11.49, 6.18 Hz), 4.20 (m, 1H), 5.86 (s, 2H), 6.11 (dd, 1H Ar, J=8.31, 2.34 Hz), 6.31 (d, 1H Ar, J=2.30 Hz), 6.66 (d, 1H Ar, J=8.28 Hz), 6.85 (s, 4H Ar).

EXAMPLE 3

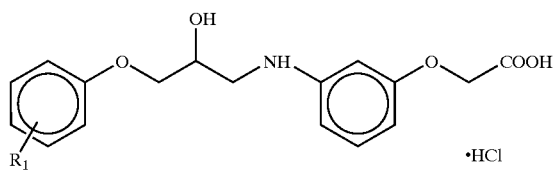

3-[(3-Phenoxy-2-hydroxypropyl)amino]phenoxyacetic Acid, Hydrochloride Salt ($R_1$=H)

A mixture of 3 g (21.56 mmol) of 3-nitrophenol, 4.3 g (22 mmol) of tert-butyl bromoacetate, 3.2 g of anhydrous potassium carbonate and 50 ml of acetone is stirred overnight at room temperature. The mixture is filtered and washed with acetone and both the filtrate and the washing product are evaporated to give a yellow oil. The oil is purified on a silica gel chromatography column using an EtOAc/cyclohexane mixture (50/50) as the eluent to give 5 g (92%) of tert-butyl 3-nitrophenoxyacetate (colourless oil). 2 g of Pd/C (10%) are added to a solution of 4.8 g (18.95 mmol) of tert-butyl 3-nitrophenoxyacetate in 20 ml of ethanol and the mixture is hydrogenated overnight at one atmosphere. The catalyst is filtered off. The solvent is evaporated off to give 3.38 g (80%) of tert-butyl 3-amidophenoxyacetate, which is chromatographed on a silica gel column using an EtOAc/cyclohexane mixture (50/50) as the eluent. A mixture of the resulting amine (0.5 g, 2.24 mmol) and 1,2-epoxy-3-phenoxypropane is heated at 70° C. overnight. After cooling, the product is washed with ethanol and the precipitate is filtered off to give 0.6 g of the tert-butyl ester. 0.6 g of this ester and 15 ml of 6 N HCl are mixed overnight at 80° C. The solvent is evaporated off and the residue is washed with an EtOH/$CH_3CN$ mixture and then recrystallized from $CH_3CN$ to give 0.36 g of a salt with the following characteristics: melting point 138–139° C.; $^1H$ NMR (DMSO-$d_6$) δ 3.82 (m, 2H), 3.96 (m, 4H), 4.06 (m, 1H), 4.72 (s, 2H), 6.88–7.00 (n, 5H Ar), 7.24–7.45 (m, 4H Ar).

EXAMPLE 4

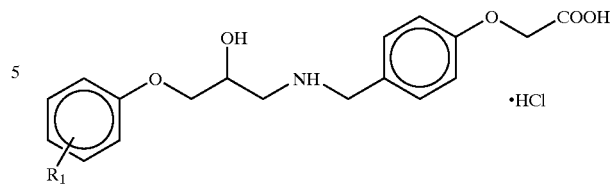

4-[(3-Phenoxy-2-hydroxypropyl)amidomethyl]phenoxyacetic Acid, Hydrochloride Salt ($R_1$=H)

A mixture of 22.16 g (0.186 mol) of 4-cyanophenol, 32.07 g (0.192 mol) of ethyl bromoacetate, 27.6 g (0.199 mol) of $K_2CO_3$ and acetone (250 ml) is stirred at room temperature for 12 hours. After filtration, the solvent is evaporated off under vacuum and the residue is partitioned between an organic phase (ethyl acetate) and an aqueous phase (water). The organic layer is dried ($MgSO_4$) and concentrated under vacuum to give 36.42 g (95%) of ethyl 4-cyanophenoxyacetate (white solid, melting point: 49–50° C.).

1.5 g of Pd/C (10%) are added to a solution of the resulting ester (4.1 g, 20 mmol) in ethanol (80 ml) and the mixture is hydrogenated under a pressure of 50 bar at room temperature for 16 hours. The catalyst is filtered off (Célite®) and the filtrate is concentrated under vacuum to give a mixture of 38% of the monobenzylamine derivative and 42% of the dibenzylamine derivative, which is chromatographed on silica gel using an EtOAc/MeOH mixture (8/2) as the eluent.

0.4 g (1.9 mmol) of the amine 16 (n=1 and R=Et) is dissolved in DNE (5 ml) containing one equivalent (0.3 g, 2 mmol) of (±)-1,2-epoxy-3-phenoxypropane and heated overnight at 80° C. After cooling, the solvent is removed under vacuum and the oily residue is triturated with $Et_2O$, filtered off and washed with EtOH and MeOH to give 0.25 g (37%) of ethyl 4-[(3-phenoxy-2-hydroxypropyl)amidomethyl]phenoxyacetate, an ester in the form of a white solid melting at 120° C., which is hydrolyzed with 6 N HCl, as described in Example 3, to give the desired derivative in the form of a white solid.

Other compounds are prepared by the technique described in Example 1 and have the following characteristics:

| Compound | $R_1$ | $R_2$ | Q | Yield % | M.p. ° C. |
|---|---|---|---|---|---|
| 5a | H | bond | fluorene | 55 | 138/9 |
| 5b | 4-OMe | " | " | 64 | 119/20 |
| 5c | 3-OH | " | " | 42 | 94/5 |
| 6a | H | " | fluorenyl | 63 | 96/7 |
| 6b | 3-OH | " | " | 58 | 282/3 |
| 7 | H | " | adamantyl | 79 | 230/1 |
| 8 | H | —$CH_2$— | " | 65 | 195 |

-continued

| Compound | R$_1$ | R$_2$ | Q | Yield % | M.p. °C. |
|---|---|---|---|---|---|
| 9 | CF$_3$ | —CH$_2$— | " | 44 | 175 |
| 10 | H | —CH$_2$—CH$_2$— | " | 47 | 170 |
| 11 | H | bond | (adamantyl) | 82 | 62/3 |
| 12 | H | —CH$_2$—CH$_2$— | " | 56 | 71 |
| 13 | H | bond | (trimethylcyclohexyl/isopropyl) | 65 | 105 |
| 14 | H | bond | (trimethylbicyclic) | 58 | 128 |
| 15 | H | bond | (trimethylcyclohexyl) | 60 | 234/5 HCl |
| 16 | 4-OMe | bond | " | 62 | 185 HCl |
| 17 | H | bond | (benzodioxane) | 58 | 87 |
| 18 | 4-OMe | bond | " | 42 | 92 |

$^1$H NMR spectra (δ) of the compounds 5 to 8

Compound 5a (maleate), δ (ppm): 3.17 (dd, 1H, J=11.97, 5.21 Hz), 3.31 (dd, 1H, J=12.0, 4.9 Hz), 3.74 (s, 2H), 4.01 (m, 3H), 6.25 (s, 2H), 6.68 (dd, 1H Ar, J=8.27, 2.06 Hz), 6.88 (m, 4H Ar), 7.10 (m, 1H Ar), 7.27 (m, 3H Ar), 7.43 (d, 1H Ar, J=7.16 Hz), 7.58 (m, 2H Ar).

Compound 5b (free base), δ (ppm): 3.16 (m, 1H), 3.30 (m, 1H), 3.69 (s, 3H), 3.73 (s, 2H), 3.90 (m, 3H), 5.16 (d, 1H, J=4.84 Hz), 5.72 (t, 1H NH, J=5.79 Hz), 6.66 (dd, 1H, J=8.27, 2.01 Hz), 6.89 (m, 5H Ar), 7.10 (dt, 1H Ar, J=7.36, 1.09 Hz), 7.25 (dt, 1H Ar, J=7.43, 0.8 Hz), 7.42 (d, 1H, J=7.26 Hz), 7.54 (d, 1H Ar, J=8.27 Hz), 7.60 (d, 1H Ar, J=7.14 Hz).

Compound 5c (maleate), δ (ppm): 3.58 (m, 2H), 3.94 (m, 4H), 4.11 (m, 1H), 6.17 (s, 2H), 6.37 (s, 1H Ar), 6.56 (d, 2H, J=7.96 Hz), 6.81 (d, 1H Ar, J=7.58 Hz), 6.97–7.23 (m, 4H Ar), 7.42 (m, 1H Ar), 7.57 (m, 2H Ar).

Compound 6a (HCl), δ (ppm): 3.54 (m, 2H), 3.85 (m, 3H), 4.15 (m, 1H), 5.64 (s, 1H), 6.75–6.92 (m, 4H Ar), 7.17–7.25 (m, 2H Ar), 7.38–7.56 (m, 4H Ar), 7.96 (m, 2H Ar), 8.14 (m, 1H Ar).

Compound 7 (HCl), δ (ppm): 1.61 (m, 5H), 1.91 (m, 6H), 2.10 (m, 4H), 2.94 (m, 1H), 3.12 (m, 1H), 3.99 (dd, 2H, J=5.08 Hz), 4.22 (m, 1H), 6.90–6.97 (m, 3H Ar), 7.29 (t, 2H Ar, J=8.29 Hz).

Compound 8 (HCl), δ (ppm): 1.59–1.92 (m, 10H), 2.41 (m, 4H), 3.62 (m, 3H), 4.03 (m, 2H), 4.56 (m, 1H), 6.92–6.99 (m, 3H Ar), 7.29 (t, 2H Ar, J=7.31 Hz).

As is apparent from the foregoing description, the invention is in no way limited to those modes of execution, embodiments and modes of application which have now been described more explicitly; on the contrary, it encompasses all the variants thereof which may occur to those skilled in the art, without deviating from the framework or the scope of the present invention.

What is claimed is:

1. A method of treating diabetes, obesity or intestinal motility disorders in an animal comprising administration of a composition comprising at least one compound of general formula I below:

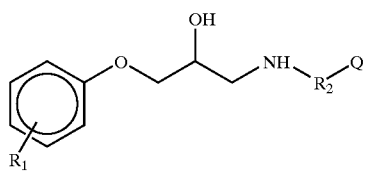

in which:

- $R_1$, a substituent in the 2-, 3- or 4-position of the phenyl group, is a hydrogen atom, a halogen atom or one of the following groups: hydroxyl; $C_1$-$C_{10}$ lower alkyl selected in particular from methyl, ethyl, propyl, isopropyl, butyl and tert-butyl groups; $C_1$-$C_{10}$-alkoxy; benzyloxy; nitro; cyano; trifluoromethyl; or amino optionally substituted (monosubstituted or disubstituted) by 1 or 2 lower alkyl radicals as defined above;
- $R_2$ is one of the following groups: —$CH_2$—, —$CH_2$—$CH_2$—, —$CH(CH_3)$—$CH_2$—, —$C(CH_3)$=$CH$—, —$C(CH_3)_2$—$CH_2$—, or a bond; and
- Q is an optionally bridged, cyclic hydrocarbon system which consists of a cyclo-alkane comprising 1, 2 or 3 rings optionally containing substituents selected from methyl, ethyl, isopropyl, propyl, butyl and tert-butyl groups, the main ring containing 5 or 6 members; in the pure state or in the form of salts with pharmaceutically acceptable acids or bases, and at least one pharmaceutically acceptable vehicle; said compound being administered at a dose ranging from 0.1 to 100 mg/kg of live weight.

2. The method according to claim 1, wherein said compound of general formula I is selected from the group consisting of compounds in which:

- $R_1$ is a hydrogen atom, a 4-O-methyl, a 3-OH or a trifluoromethyl group;
- $R_2$ is a bond or one of the following groups: —$CH_2$— or —$CH_2$—$CH_2$.

3. The method according to claim 1, wherein said composition further comprises $\beta_1$ or $\beta_2$-adrenergic products.

4. The method according to claim 1, wherein said composition is administered orally or sublingually.

5. The method according to claim 4, wherein said composition is formulated as tablets, capsules gelatin capsules or syrup.

6. The method according to claim 1, wherein said composition is administered via the intranasal route, the transdermal route or via parental routes.

7. The method according to claim 6, wherein said composition is formulated as sterile solution, sterile suspension or skin patch.

8. The method according to claim 1, wherein said composition is administered at a dose ranging from 1 to 10 mg/kg of live weight.

* * * * *